US008986237B2

(12) United States Patent
Goudaliez et al.

(10) Patent No.: US 8,986,237 B2
(45) Date of Patent: Mar. 24, 2015

(54) METHODS OF MAKING AND USING FILTERING UNIT FOR A VIRUCIDE SUBSTANCE

(75) Inventors: Francis Goudaliez, Faches-Thumesnil (FR); Thierry Verpoort, Mouvaux (FR)

(73) Assignee: Macopharma, Mouvaux (FR)

( * ) Notice: Subject to any disclaimer, the term of this patent is extended or adjusted under 35 U.S.C. 154(b) by 690 days.

(21) Appl. No.: 13/089,636

(22) Filed: Apr. 19, 2011

(65) Prior Publication Data

US 2011/0192798 A1 Aug. 11, 2011

Related U.S. Application Data

(63) Continuation of application No. 12/053,929, filed on Mar. 24, 2008, now abandoned, which is a continuation of application No. 10/111,143, filed as application No. PCT/FR00/02900 on Oct. 18, 2000, now abandoned.

(30) Foreign Application Priority Data

Oct. 20, 1999 (FR) .................................... 99 13089

(51) Int. Cl.
*A61M 37/00* (2006.01)
*B01D 39/16* (2006.01)
*A61L 2/00* (2006.01)
*A61M 1/36* (2006.01)

(52) U.S. Cl.
CPC ........... *B01D 39/1623* (2013.01); *A61L 2/0017* (2013.01); *A61M 1/3686* (2014.02)
USPC ...................................................... 604/6.01

(58) Field of Classification Search
CPC ............ A61M 1/3679; A61M 1/3633; A61M 2202/0439; A61M 2202/005; A61M 2202/0247; A61M 2202/0413
USPC ......... 604/4.01–6.16; 210/645, 490, 505–508
See application file for complete search history.

(56) References Cited

U.S. PATENT DOCUMENTS

| | | | |
|---|---|---|---|
| 4,159,954 A | 7/1979 | Gangemi | 210/446 |
| 4,276,170 A | 6/1981 | Vaillancourt | 210/436 |
| 4,701,267 A | 10/1987 | Watanabe et al. | 210/806 |
| 4,925,572 A | 5/1990 | Pall | 210/767 |
| 4,985,153 A | 1/1991 | Kuroda et al. | 210/782 |
| 5,234,593 A | 8/1993 | Kuroki et al. | 210/496 |
| 5,478,470 A | 12/1995 | Fukuda et al. | 210/500.1 |
| 5,639,376 A * | 6/1997 | Lee et al. | 210/645 |
| 5,665,233 A | 9/1997 | Fukuda et al. | 210/483 |
| 5,858,641 A * | 1/1999 | Shanbrom | 435/2 |
| 6,197,207 B1 | 3/2001 | Chapman et al. | 210/767 |
| 6,328,167 B1 | 12/2001 | Seshimoto et al. | 210/456 |
| 7,374,870 B2 * | 5/2008 | Herman et al. | 435/2 |

FOREIGN PATENT DOCUMENTS

| | | | | |
|---|---|---|---|---|
| WO | WO 95/16348 | 6/1995 | | A01N 1/02 |
| WO | WO 98/22151 | 5/1998 | | A61L 2/18 |

* cited by examiner

*Primary Examiner* — Philip R Wiest
(74) *Attorney, Agent, or Firm* — Baker Botts L.L.P.

(57) ABSTRACT

A filtering unit for removing a virucidal substance from a biological fluid including an outer casing having at least one input aperture and at least one output aperture. The outer casing including a filter medium, which separates the filtration unit into an input compartment and an output compartment. The filter medium includes at least one hydrophilic material able to absorb or adsorb the virucidal substance. The at least one hydrophilic material includes either porous nonwoven material or a porous membrane.

14 Claims, 2 Drawing Sheets

METHODS OF MAKING AND USING FILTERING UNIT FOR A VIRUCIDE SUBSTANCE

RELATED APPLICATION

This application is a continuation of U.S. application Ser. No. 12/053,929 filed Mar. 24, 2008 now abandoned; which is a continuation of U.S. application Ser. No. 10/111,143, filed Apr. 19, 2002 now abandoned, which is a U.S. national stage application of International Application No. PCT/FR00/02900 filed Oct. 18, 2000, which designates the United States of America, and claims priority to French application number FR99/13089 filed Oct. 20, 1999. The contents of these applications are hereby incorporated by reference herein in their entirety by this reference.

FIELD OF THE INVENTION

The invention relates t a filtration unit intended to remove a virucidal substance present in a biological fluid.

It typically applies to the case where the virucidal substance has previously been added to a biological fluid, in particular blood plasma, intended to be transfused into a patient. The aim of this addition is to subject the biological fluid to a viral inactivation treatment prior to its transfusion into the patient, so as to inactivate any viruses infecting the biological fluid.

BACKGROUND

A conventional technique for viral inactivation of plasma uses a colouring substance as a virucidal substance, for example methylene blue or one of its derivatives.

The principle of this technique is based on photochemical reactions between the colouring substance and the viral DNA or RNA which may be present in the biological fluid.

Exposure of the colouring substance to light brings about a photochemical reaction which transmits energy to the DNA and RNA molecules so that the virus is inactivated.

During these photochemical reactions, the colouring substance is not removed so that it remains in the biological fluid after exposure to light.

After the use of this viral inactivation technique, a very small amount of the colouring substance may be left in the biological fluid and thus be transfused into the patient at the same time as the biological fluid.

However, recent studies seem to show the possible toxicity of certain colouring substances used, and in particular methylene blue, when they are injected into the patient.

So much so that many countries are demanding the systematic removal of colouring substances prior to injection of the biological fluid into the patient.

SUMMARY OF THE INVENTION

The invention therefore aims to propose a filtration unit which makes it possible to remove substantially all the virucidal substance present in the biological fluid while leaving the composition of the biological fluid substantially unchanged during the filtration.

To that end, the object of the invention is a filtration unit intended to remove a virucidal substance present in a biological fluid, comprising an outer casing provided with at least one input aperture and at least one output aperture, the casing containing a filter medium which delimits two compartments, respectively input and output, of the filtration unit, in which the filter medium is produced from at least one hydrophilic material in the form of a porous non-woven material and/or a porous membrane capable of absorbing and/or adsorbing the virucidal substance.

According to one embodiment, the mean porosity of the filter medium is defined so that the contact area between the biological fluid and the filter medium is sufficient to remove substantially all the virucidal substance while leaving the composition of the biological fluid substantially unchanged during its passage through the filter medium, namely being between 1 µm and 15 µm.

In a variant, the mean diameter of the fibres of the porous non-woven material is between 0.5 µm and 5 µm.

The input compartment and/or the output compartment communicate with the outside of the filtration unit by means of an input, respectively output, tube.

The hydrophilic material of the filter medium is chosen in particular from amongst the naturally hydrophilic materials or the materials, in particular based on plastic material, made hydrophilic, for example from amongst the polymers and/or the copolymers based on polyester, acrylonitrile or polyvinylidene fluoride.

According to one embodiment, the filter medium comprises a number of layers of hydrophilic material, identical or different in nature to one another, with a contact area identical or different to one another.

The filter medium has for example a thickness between 1 and 10 millimeters.

According to one embodiment, the outer casing of the filtration unit is rigid.

According to another embodiment, the outer casing of the filtration unit is flexible.

In a variant, the flexible casing is formed from two sheets of flexible plastic material connected together on their periphery, the filter medium being held in a flexible and impervious frame delimiting, with the filter medium, the input and output compartments of the filtration unit.

The flexible frame is, for example, formed from two flexible sheets perforated between them between which the filter medium is placed, the flexible sheets being fixed to one another in the region of the periphery of the filter medium and also with the sheets forming the outer casing, in the region of the periphery of the outer casing of the filtration unit.

The fixing of the sheets forming the flexible frame is then a weld seam made through the filter medium.

According to one embodiment, the output compartment is kept clear of the filter medium by the presence of one or more spacing rods disposed between the filter medium and the flexible outer casing, inside the output compartment.

The spacing rod or rods are produced from flexible tubes welded for example at the inner wall of the sheet of the outer casing.

Other objects and advantages of the invention will emerge during the description which follows with reference to the accompanying drawings.

DETAILED DESCRIPTION

Figure 1:
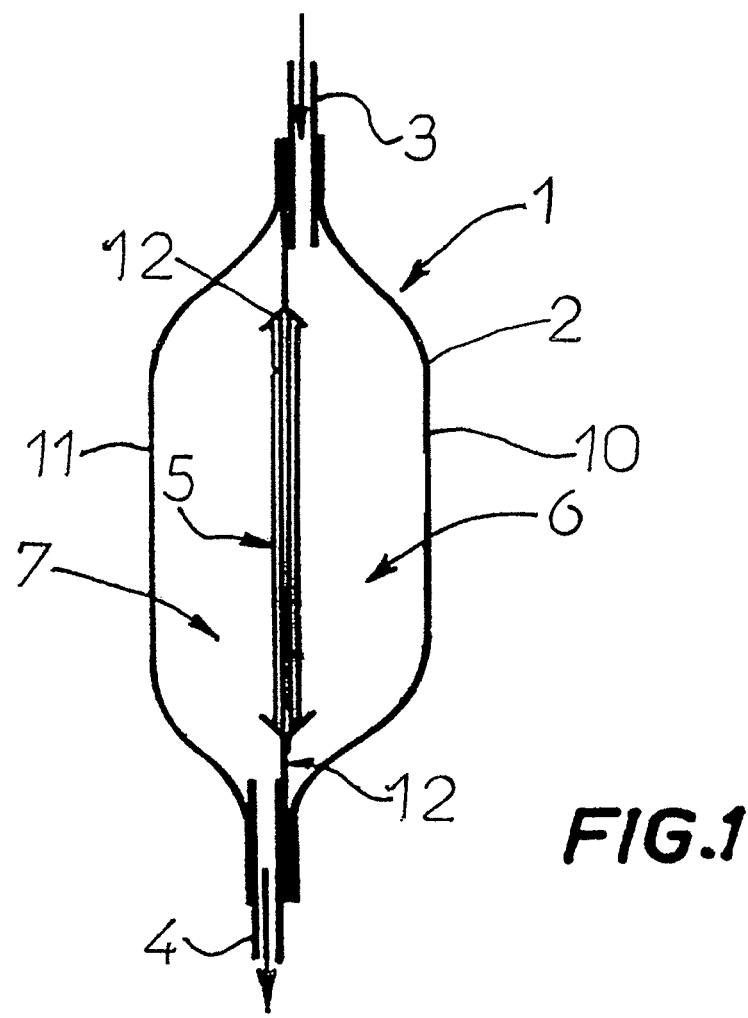
FIG. 1 depicts, in side view and longitudinal section, one embodiment of the filtration unit comprising a flexible outer casing.

A filtration unit 1 intended to remove a virucidal substance present in a biological fluid comprises typically an outer casing 2 provided with at least one input aperture 3 and at least one output aperture 4, the casing containing a filter medium 5 which delimits two compartments, respectively input 6 and output 7, of the filtration unit 1.

In the description, the words "input" and "output" are defined with respect to the direction of movement of the biological fluid in the filtration unit 1 (see the arrows shown in FIG. 1).

According to one particular embodiment, the biological fluid is blood or a blood compound, in particular blood plasma, and the virucidal substance is methylene blue or one of its derivatives.

Prior to its passage into the filtration unit 1, the biological fluid has undergone a viral inactivation treatment by means of the virucidal substance which was added to the biological fluid.

This treatment, generally used at the blood transfusion centre, will not be described further here.

The filtration unit 1 is intended to be integrated, in particular by means of tubes, respectively input 8 and output 9, into a system comprising for example bags for medical use, tubes, clamps or other filters (for example to remove leukocytes from the biological fluid).

In such a system, the filtration unit 1 is disposed on the flow path of the biological fluid so that the biological fluid with the virucidal substance added enters the filtration unit 1 by the input aperture 3 and the biological fluid free from the virucidal substance is delivered by means of the output aperture 4.

One particular example of such a system is a transfusion line of a bag containing a biological fluid to be transfused into a patient. In such a line, the filtration unit 1 is connected by its input 3 to the bag containing the biological fluid with the virucidal substance added and by its output 4 to means of transfusion of the biological fluid free from virucidal substance.

These various systems are not described further inasmuch as they comprise the filtration unit 1 according to the structure described here.

A description is now given of a first embodiment of the filtration unit 1 comprising a flexible outer casing 2 formed by the assembly of two sheets of flexible plastic material 10, 11 connected to one another, for example by welding, on their periphery (FIG. 1).

This outer casing contains a filter medium designated generally by the reference 5, the structure of which will be described in more detail below.

The filter medium 5 is held in a flexible and impervious support frame 12 and delimits two compartments, respectively input 6 and output 7, of the filtration unit 1.

The input compartment 6 communicates with the outside of the filtration unit 1 by means of an input tube 8 which is used to fill it with the biological fluid with the virucidal substance added.

The output compartment 7 communicates with the outside of the filtration unit 1 by means of an output tube 9 which delivers the biological fluid free from virucidal substance.

The structure of the filtration unit 1 thus allows the biological fluid with the virucidal substance added to be received in the input compartment 6 via the input aperture 3, to pass through the filter medium 5 so that the virucidal substance is absorbed and/or adsorbed thereby, and then the biological fluid free from virucidal substance is received in the output compartment 7 in order to be delivered via the output aperture 4.

According to one embodiment, the input tubes 8 and/or output tubes 9 are flexible, and can be cut and welded.

Where a collecting bag is associated with the output tube 9, this embodiment makes it possible, after separation of the filtration unit 1 by cutting and welding of the output tube 9, to obtain a bag full of biological fluid free from virucidal substance. Such a bag can then be used conventionally, for example for transfusion into a patient.

A first level of sealing of the filtration unit 1 is provided between the filter medium 5 and the flexible frame 12 where no tube passes.

A second level of sealing is provided at the periphery of the filtration unit 1 where the two outer sheets 10, 11, the periphery of the flexible frame 12 and the passage of the input tube 8 and output tube 9 come together.

This second level of sealing can be provided by the known techniques for connecting plastic materials, for example by high-frequency welding.

Figure 2:
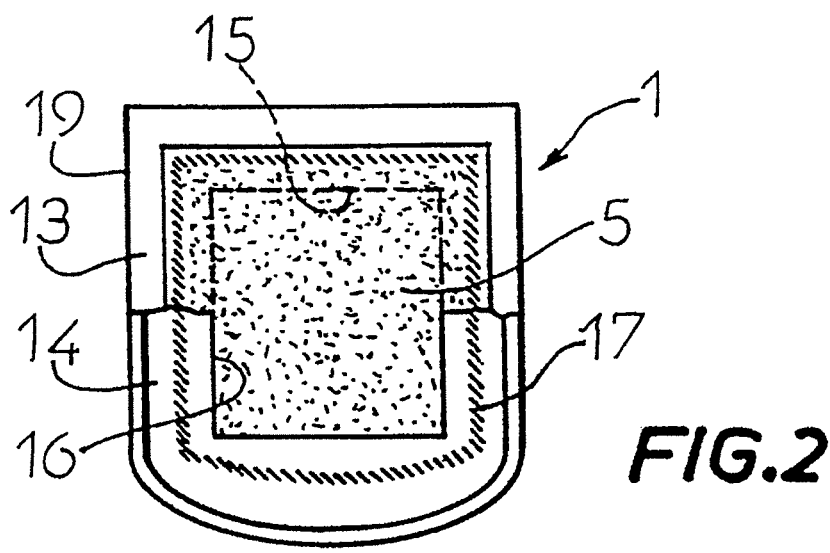
FIG. 2 depicts, in front view and partial longitudinal section, the embodiment of FIG. 1 showing in particular the assembly of the filter medium in a flexible frame.
Figure 3:
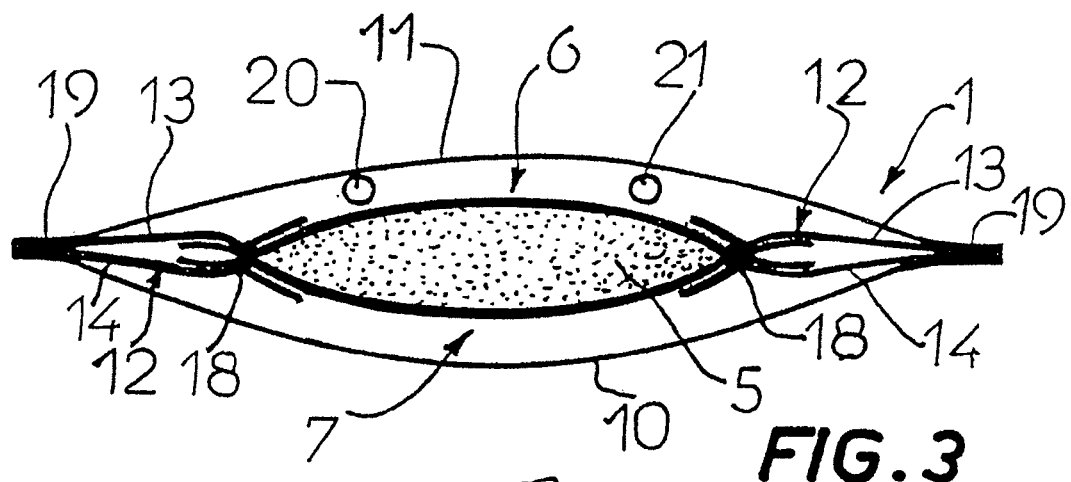
FIG. 3 depicts, in top view and transverse section, the embodiment of FIG. 1, showing in particular the assembly of the frame containing the filter medium in the outer casing.
Figure 4:
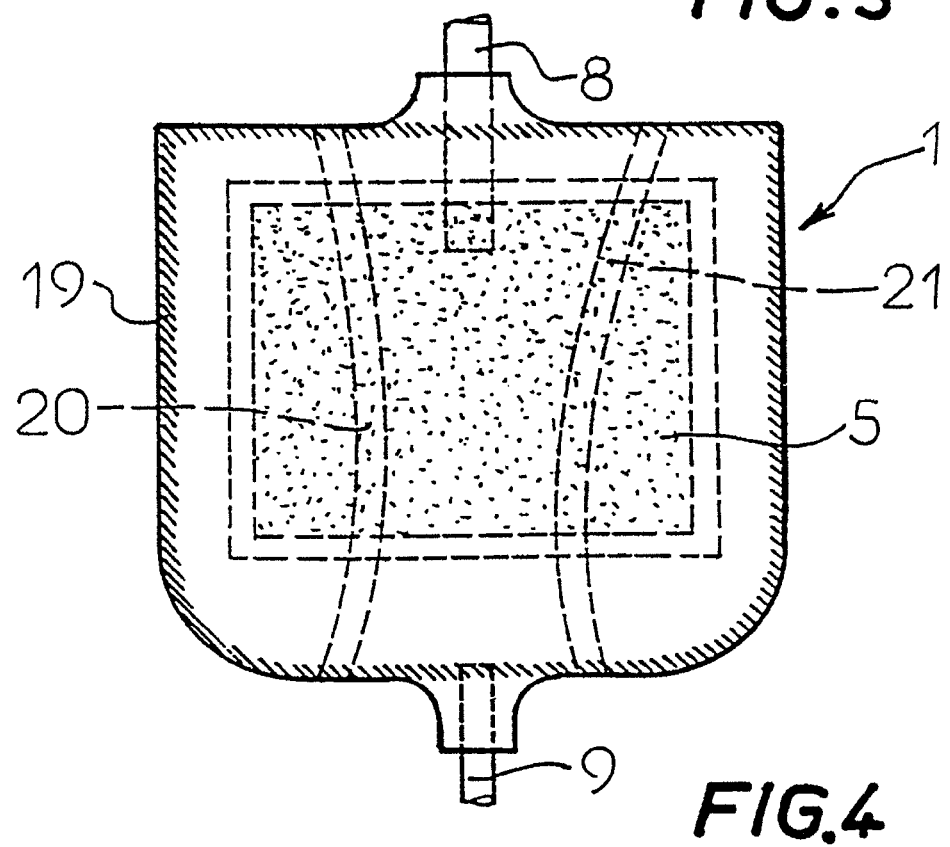
FIG. 4 depicts, in front view and partial longitudinal section, the filtration unit of FIG. 3 in which the spacing rods appear.

The implementation of the assembly of the filtration unit 1 is now described with reference to FIGS. 2 to 4.

The flexible frame 12 is formed by an assembly of two sheets 13, 14, for example plasticised sheets, between which the filter medium 5 is placed.

These two sheets 13, 14 are perforated in their central part and each have at least one opening 15, 16 allowing passage of the biological fluid to be filtered.

The two sheets 13, 14 are fixed to one another preferably in the region of the periphery of the filter medium 5, for example by a weld seam 17, made through the filter medium 5, providing both the fixing of the filter medium 5 and also the sealing of the unit 1.

The welding of the sheets 13, 14 through the filter medium 5 causes a compression 18, forming an impervious seam around the filter medium 5.

The periphery 19 of the flexible frame 12 is also welded with the outer sheets 10, 11 forming the outer casing 2 of the filtration unit 1, these being welded to one another over their entire circumference and in the region of their periphery, thus providing the sealing of the unit 1.

In order to avoid the filter medium 5 sticking against the outer casing 2, and thus interfering with the flow of the biological fluid into the output compartment 7, two spacing rods 20, 21 are placed inside the output compartment 7, between the filter medium 5 and the outer casing 2.

The two rods 20, 21 keep the output compartment 7 clear of the filter medium 5 and thus avoid the filter medium 5 being flattened against the inner wall of the outer sheet 2.

The rods 20, 21 can be produced from flexible tubes welded for example at the inner wall of the sheet of the outer casing 2, for example in the region of the peripheral weld 19 of the filtration unit 1.

It is self-evident that the number of spacing rods can vary, depending for example on the dimensions of the filtration unit 1.

For example, provision of a single spacing rod folded so as to form a loop inside the output compartment 7 can be envisaged.

Preferably, flexible rods are used, in order not to interfere with the possibilities of folding the filtration unit 1.

In a second embodiment (not depicted), the filtration unit 1 comprises a rigid outer casing 2, for example made of a rigid plastic material such as polycarbonate.

There will now be described in more detail the structure and implementation of the filter medium 5 capable of removing substantially all the virucidal substance while leaving the composition of the biological fluid substantially unchanged during the filtration.

In a first embodiment, the filter medium 5 is produced from at least one hydrophilic material in the form of a porous non-woven material.

In a second embodiment, the filter medium 5 is produced from at least one hydrophilic material in the form of a porous membrane.

In a third embodiment, the filter medium 5 is produced from a hydrophilic material in the form of at least one porous membrane which is inserted between a number of layers of hydrophilic material in the form of a non-woven material.

In these three embodiments, the hydrophilic material is capable of absorbing and/or adsorbing the virucidal substance, in particular by affinity between the virucidal substance and the hydrophilic material.

Various materials can be used for producing the filter medium depending on the nature of the fluid to be filtered and that of the biological fluid.

The choice of materials usable in the filtration unit according to the invention is however limited by the fact that they must not prevent, in particular by affinity, the passage of the cellular or non-cellular constituents of the biological fluid.

In other words, the material forming the filter medium must be capable of absorbing and/or adsorbing the virucidal substance but not the constituents of the biological fluid.

In the case of treatment of a blood plasma containing methylene blue, the following can be cited amongst the possible materials: the polymers and/or the copolymers based on polyester, acrylonitrile or polyvinylidene fluoride.

These polymeric products are generally not naturally hydrophilic and must be treated by physical and/or chemical methods, in order to give them said hydrophilic properties.

These treatments consist for example in grafting hydrophilic substituents, for example hydroxyl or carboxylic type groups, onto the polymer, according to known methods.

Such polymers made hydrophilic by physical and/or chemical treatment are available on the market.

The hydrophilic nature of the material forming the filter medium 5 allows a good wettability of the filter medium during passage of the biological fluid, which allows in particular a better flow of the biological fluid through the filtration unit 1 but also an improvement in the filtration efficiency.

The porosity characteristics of the filter medium allow the passage of the biological fluid through the filtration unit while leaving the composition of the biological fluid substantially unchanged.

To that end, the mean size of the pores of the filter medium is chosen according to the biological fluid to be treated. For example, for the filtration unit 1 to allow the constituents of whole blood to pass, the mean size of the pores can be of the order of or greater than 7 $\mu$m. In the case of blood plasma, the mean size of the pores can be smaller, for example of the order of 4 $\mu$m, on account of the absence of cellular constituents in the plasma.

During passage of the biological fluid with the virucidal substance added through the filter medium 5, the contact area between the biological fluid and the filter medium must be sufficient to remove substantially all the virucidal substance while leaving the composition of the biological fluid substantially unchanged.

In the first embodiment, this characteristic is advantageously obtained by means of the use of a non-woven material which has, through its structure, a large contact area for a small volume.

Contact area between the biological fluid and the filter medium means the area over which the absorption and/or adsorption of the virucidal substance by the porous material can take place. It is self-evident that this area is a function in particular of the area of the filter medium, its porosity, its thickness and the diameter of the fibres of the non-woven material.

Thus, by changing the diameter of the fibres, the porosity of the non-woven material and the thickness of the filter medium 5 it composes, access can be obtained to a wide range of contact areas which makes it possible to remove substantially all the virucidal substance while leaving the composition of the biological fluid substantially unchanged.

By way of example, there can be cited a filter medium 5 formed from a non-woven material made of polyester having a thickness of the order of 5 mm, a mean porosity of the order of 8 $\mu$m and a mean fibre diameter of the order of 2 $\mu$m, allowing the removal of a concentration of 1 $\mu$m of methylene blue in 250 ml of blood plasma.

It should be noted however that these values can vary to a great extent, in particular according to the time of contact between the filter medium and the biological fluid, that is to say the filtration speed.

In the second embodiment, a porous membrane is used as the filter medium 5 to absorb and/or adsorb the virucidal substance present in the biological fluid.

In one particular example, such a membrane is made of polyvinylidene fluoride and with a pore size calibrated to a value between 1 and 15 $\mu$m.

In the third embodiment, the filter medium 5 can combine the two materials used in the preceding embodiments, namely comprise a number of layers of hydrophilic material in the form of a porous non-woven material and one or more porous membranes. The material and/or the structure of the material forming these layers can then be identical or different to one another.

The layers are then disposed, for example contiguously, next to one another in the filtration unit so that the biological fluid passes through them successively during the filtration.

In one particular example, there can be cited a filter medium 5 formed from a superposition of layers formed respectively of a "spunbond" type polyester non-woven material, a "meltblown" type polyester non-woven material, one or more polyvinylidene fluoride membranes, a "meltblown" type polyester non-woven material and a "spunbond" type polyester non-woven material.

The words "spunbond" and "meltblown" mean two of the conventional methods of forming a layer of non-woven material directly from the polymer, namely respectively either by forming continuous monofilaments or by blowing the polymer in the molten state into irregular filaments.

As these techniques are conventional, they will not be detailed further here.

In this embodiment, the two outer layers of "spunbound" non-woven material are identical and serve respectively as a pre- and post-filter. Furthermore, they have the function of improving the weldability of the filter medium 5 onto the casing 2 of the filtration unit 1.

The two layers of "meltblown" non-woven material and the membrane or membranes placed between them form more particularly the filter medium 5 capable of absorbing and/or adsorbing the virucidal substance.

Furthermore, the two layers of "meltblown" non-woven material are identical and have the function of protecting the membrane or membranes.

The invention claimed is:

1. A method for eliminating a virucidal substance from a biological fluid comprising:
    passing the biological fluid through a filter medium produced from a naturally non-hydrophilic polymer or copolymer that has been treated by a chemical or physical method to produce a hydrophilic polymer or copolymer, the hydrophilic polymer or copolymer in the form of a membrane, capable of absorbing or adsorbing the virucidal substance and having a porosity that allows passage of the biological fluid through the filter medium.

2. The method according to claim 1, wherein the biological fluid comprises blood, serum or plasma.

3. The method according to claim 1, wherein the virucidal substance comprises methylene blue.

4. The method according to claim 2, wherein the methylene blue has a concentration of 1 μM.

5. The method according to claim 1, wherein the hydrophilic polymer or copolymer comprises polyester that has been treated by a chemical or physical method to render it hydrophilic.

6. The method according to claim 1, wherein the hydrophilic polymer or copolymer comprises acrylonitrile that has been treated by a chemical or physical method to render it hydrophilic.

7. The method according to claim 1, wherein the hydrophilic polymer or copolymer comprises polyvinylidene fluoride that has been treated by a chemical or physical method to render it hydrophilic.

8. The method according to claim 1, wherein the hydrophilic polymer or copolymer comprises polyvinylidene fluoride and polyester that have both been treated by a chemical or physical method to render both hydrophilic.

9. The method according to claim 1, wherein the filter medium has a mean porosity of between 1 μm and 15 μm.

10. The method according to claim 1, wherein the hydrophilic polymer or copolymer is in the form of non-woven fibers.

11. The method according to claim 1, wherein the hydrophilic polymer or copolymer is in the form of one or more porous non-woven materials and one or more porous membranes.

12. The method according to claim 1, wherein the naturally non-hydrophilic polymer or copolymer has been treated by grafting hydrophilic substituents to render it hydrophilic.

13. The method according to claim 12, wherein the hydrophilic substituents comprise a hydroxyl or a carboxylic group.

14. The method according to claim 1, wherein the membrane is capable of absorbing or adsorbing the virucidal substance, while allowing the passage of cellular constituents of the biological fluid.

* * * * *